United States Patent [19]

Wernicke et al.

[11] Patent Number: 4,808,270

[45] Date of Patent: Feb. 28, 1989

[54] PROCESS AND APPARATUS FOR THE PREPARATION OF ETHER

[75] Inventors: Hans-Juergen Wernicke, Geretsried; Reinhard Glatthaar; Nikolaus Buckl, both of Munich, all of Fed. Rep. of Germany

[73] Assignee: Linde Aktiengesellschaft, Wiesbaden, Fed. Rep. of Germany

[21] Appl. No.: 5,820

[22] Filed: Jan. 21, 1987

Related U.S. Application Data

[63] Continuation-in-part of Ser. No. 781,811, Sep. 3, 1985, abandoned.

[30] Foreign Application Priority Data

Sep. 29, 1984 [DE] Fed. Rep. of Germany ....... 3435936

[51] Int. Cl.$^4$ .......................... B01D 3/14; C07C 41/42
[52] U.S. Cl. ......................................... 203/39; 203/94; 203/97; 203/98; 203/DIG. 23; 202/204; 568/697; 568/699; 568/913
[58] Field of Search ................... 203/94, DIG. 25, 39, 203/97, 98, 91, DIG. 23; 202/182, 202, 204; 568/697, 699, 918, 913

[56] References Cited

U.S. PATENT DOCUMENTS

| | | | |
|---|---|---|---|
| 4,299,999 | 11/1981 | Mikitenko et al. | 203/70 |
| 4,302,298 | 11/1981 | Mikitenko et al. | 203/94 |
| 4,334,964 | 6/1982 | Prezelj et al. | 568/699 |
| 4,440,963 | 4/1984 | Childs | 568/699 |
| 4,504,688 | 3/1985 | Herwig et al. | 568/699 |
| 4,544,776 | 10/1985 | Osterburg | 568/697 |

FOREIGN PATENT DOCUMENTS

| | | | |
|---|---|---|---|
| 0075136 | 3/1983 | European Pat. Off. | 568/699 |
| 1473263 | 5/1977 | United Kingdom . | |
| 2134905 | 8/1984 | United Kingdom | 568/699 |

OTHER PUBLICATIONS

Torck et al., "Methanol For Motor Fuel Via the Ethers Route", CEP, Aug. 1982, pp. 36–45.
Soviet Inventions Illustrated, Section CH, Week B, 49, 23, Jan. 1980, Derwent Publications Ltd., London; H 06 -SU 652 169.

*Primary Examiner*—Kenneth M. Schor
*Assistant Examiner*—V. Manoharan
*Attorney, Agent, or Firm*—Millen & White

[57] ABSTRACT

For the preparation of an ether, e.g., tertiary amyl methyl ether, an olefin-containing feed stream is catalytically etherified with an alcohol, e.g., methyl alcohol. The etherification product is fractionally distilled into an overhead fraction containing essentially unreacted, light hydrocarbons and unreacted alcohol and into a bottoms fraction containing essentially the desired ether. The overhead fraction is condensed and cooled to resultant immiscible phases, of which one contains essentially the alcohol and the other contains essentially the hydrocarbons, are removed separately from each other. Water may be added to the overhead stream to facilitate the formation of the two liquid phases.

20 Claims, 2 Drawing Sheets

PROCESS AND APPARATUS FOR THE PREPARATION OF ETHER

CROSS-REFERENCE TO RELATED APPLICATION

This is a continuation-in-part of application Ser. No. 781,811, filed Sept. 30, 1985, now abandoned, the contents being incorporated by reference herein.

BACKGROUND OF THE INVENTION

This invention relates to an improvement in a system for the production of an ether wherein an olefin-containing feed stream is catalytically etherified with an alcohol, and the product formed during etherification is distilled into: an overhead fraction of unreacted, light hydrocarbons and unreacted alcohol, and a bottoms fraction of the desired ether. The overhead fraction is then condensed, and the alcohol is thereafter separated from this condensate.

Suitable additives for gasoline include, besides the conventional methyl tert-butyl ether, higher tertiary ethers as well, an example being the tert amyl homolog. The purpose of adding ether is primarily to raise the octane number of the fuel. The ethers are produced by selective catalytic etherification of the corresponding olefinic fractions with alcohol especially methanol.

In a conventional method of this type (Chemical Engineering Progress, August 1982, pages 36–45), a $C_5$ hydrocarbon feed stream is mixed with methanol and introduced into the reactor in a presence of a selective catalyst to convert a fraction of the feedback to tertiary amyl methyl ether (TAME). The reaction mixture discharged from the reactor, containing hydrocarbons, ether and methanol, is thereafter introduced into a distillation column to separate the methanol by azeotropic distillation whereby there is obtained an overhead fraction containing the unreacted methanol as well as part of the unreacted $C_5$ hydrocarbons, and a bottoms product containing the TAME as well as the remaining unreacted $C_5$ hydrocarbons. The methanol in the overhead is separated from the $C_5$ hydrocarbons by a water scrubbing step, and the water is thereafter separated from the methanol in a distillation column.

In this process, the separation of unreacted methanol, requiring both a water scrubbing step and a methanol/water distillation step, is relatively expensive.

SUMMARY OF THE INVENTION

An object of one aspect of the invention is to provide an improved process of the type discussed above, including, in particular, a more efficient method for the continuous recovery of excess alcohol.

An object of another aspect of the invention is to provide associated apparatus for this method.

Upon further study of the specification and appended claims, further objects and advantages of this invention will become apparent to those skilled in the art.

To attain the first mentioned object of this invention, the process comprises cooling the overhead condensate to below the single phase saturation temperature to obtain two phases, of which one contains essentially, if not most of the hydrocarbons, and discharging the two phases separately from each other.

It has been discovered within the context of this invention that the distillate formed during condensation of the overhead fraction is rapidly split into immiscible liquid under cooling, thus obtaining a phase containing the largest portion of the alcohol. During cooling, there are formed a heavier bottom layer containing, in essence, unreacted alcohol, and a top layer containing essentially the unreacted hydrocarbons. The two liquid phases are removed separately from each other from a tank, preferably designed as a decanting vessel.

Consequently, by the process of this invention, the recovery of the alcohol is greatly facilitated, and the separation of the two phases takes place continuously.

In a preferred embodiment of the process of this invention, the immiscible phase containing essentially the alcohol is at least is part recycled into the etherification reactor.

It is advantageous to cool the overhead with a cold stream from the gas separation section of an installation for the thermal or catalytic cracking of hydrocarbons, or from a low-temperature gas separation facility.

The overhead fraction is advantageously cooled to a temperature of $-60°$ C. to $+50°$ C. prior to separation of the two phases. It is generally necessary to subcool the overhead stream to approximately $-60°$ C. to 31 43° C., preferably to $-50°$ C., in order to form two immiscible phases, i.e. to below the single-phase saturation curve.

According to a preferred further development of the process of this invention, water is admixed to the overhead stream prior to or during phase separation. In particular, the proportion of water admixed is between 0.01 and 2% by weight of the overhead fraction. This admixture is different in kind from a water contacting step, involving much higher quantities of water which is not required in this invention to separate the alcohol from the $C_5$ fraction in the overhead fraction. After such a water-contacting step, the resultant aqueous phase is conventionally separated in a distillation column into alcohol and water phases, a separation step which can be advantageously avoided by the present invention.

The introduction of water effects improved separation of the alcohol and the hydrocarbons, and permits phase separation at a higher temperature. Most of the water is withdrawn with the alcohol phase. This water causes no significant problems even when the alcohol is recycled into the etherification reactor since the water does not affect the etherification significantly, leading merely to the formation of a minor quantity of higher alcohols which are removed during distillation in the bottoms product. In turn, these higher alcohols improve the burning characteristics of gasoline.

It proved to be advantageous if, according to another development of the process of this invention, distillation and phase separation are carried out under a pressure of 1–20 bar, preferably 1.5–3 bar.

In a preferred embodiment of the process of this invention, the ether is separated from the bottoms product of the distillation in the pure form or in a mixture with a portion of the unreacted hydrocarbons. Thus, the ether is conventionally admixed to regular gasoline either in the pure form or with the unreacted hydrocarbons.

It is advantageous in some cases if a least a portion of the immiscible phase containing the hydrocarbons (the top layer) is admixed with the distillation bottoms product. This embodiment is utilized when the unreacted feed hydrocarbons are used to dilute the ether.

It is also advantageous to introduce at least a portion of the immiscible phase containing essentially the hydrocarbons into the distillation as reflux liquid. The recycled hydrocarbons enhance complete separation of the alcohol as the overhead product during distillation, so that the ether-containing bottoms product can be adjusted to be either free of alcohol or to contain a tolerable residual content, e.g., up to 1 wt. %.

In a preferred further embodiment of the process of this invention, methanol is utilized as the alcohol. The process of the invention is, in addition, also usable with the employment of other alcohols, for example, ethanol, for the preparation of ethyl tertiary amyl ether.

In an advantageous further embodiment of the process of this invention, the feed stream contains essentially C5 hydrocarbons. In this connection, it is particularly advantageous if, as is furthermore proposed, a conventional catalyst is utilized during the etherification which is selective for the formation of tertiary amyl methyl ether (TAME). Besides, the process of this invention can also be utilized for the manufacture of C4 and C6+ ethers, produced analogously from the corresponding olefin and methanol or higher alcohols.

It is also possible if the feed stream employed is a light gasoline fraction from a thermal or catalytic cracking stage.

In a preferred further embodiment of the process of this invention, etherification is conducted at a temperature of +40° to +120° C. and under an absolute pressure of 1.2–20 bar.

Preferably, at least part of the heat of reaction liberated during etherification is used to heat a portion of or the entire feed stream for etherification.

An apparatus for performing the process of this invention comprises a reactor having a feed conduit and a discharge conduit, a distillation column connected to the discharge conduit, this column having exit conduits for an overhead fraction and a bottoms fraction, a condenser located in the exit conduit for the overhead fraction, and a downstream condensate tank, the latter tank being a phase separator for two liquid having differing densities, and that one withdrawal conduit is provided for each of the two phases. Suitably, the two withdrawal conduits terminate in superposed relationship into the phase separator.

BRIEF DESCRIPTION OF THE DRAWINGS

The invention, as well as additional details of the invention, will be described in greater detail with reference to schematically illustrated examples for the product of TAME.

In the drawing.

DETAILED DESCRIPTION OF THE DRAWINGS

Figure 1:
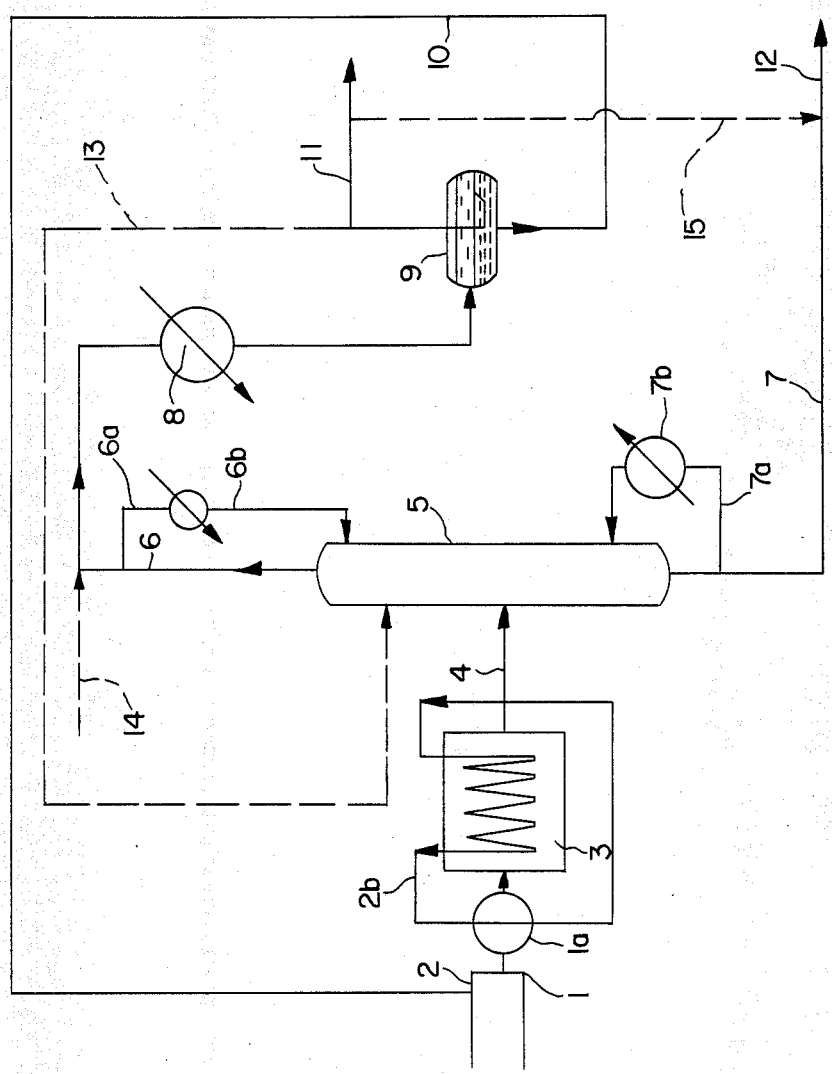
FIG. 1 is a flow chart of a preferred embodiment of the invention.

The process illustrated in FIG. 1 is used for the production of TAME. TAME is utilized, for example, as an additive to raise the anti-knock quality of low-lead and-/or unleaded motor gasolines. A hydrocarbon feed stream 1, for example a C5 fraction of pyrolysis gasoline or a corresponding cut from a fluidized cat cracker, is introduced together with methanol (conduit 2) into a preheating chamber 2a, where it is preheated by heat exchange with the hot coolant in conduit 2b that is removing the heat of reaction from an etherification reactor 3. The etherification reactor 3 contains a catalyst selectively effective for the formation of TAME, for example polystryrene resin in the H form, sulfonated phenol-formaldehyde resins, or sulfonated carbon.

In etherification reactor 3, the hydrocarbon feed stream 1 is etherified with the methanol. The primary reaction taking place is the reaction of 2-methyl-1-butene (gamma-amylene) and 2-methyl-2-butene (beta-isoamylene) with methanol to TAME. The reaction conversion rate is about 65%. With suitable selection of the catalyst, there is essentially no reaction of all of the other components of the C5 fraction with methanol. The following secondary reactions occur to a minor extent:

isoamylene + $H_2O$ = tert-amyl alcohol
methanol + methanol = dimethyl ether + $H_2O$
2 isoamylene = diisoamylene A portion of the hydrocarbon feedstock and of the methanol flows through the etherification reactor 3 without reaction. Accordingly, a product stream 4 is withdrawn from etherification reactor 3 which contains TAME as well as the above-mentioned by-products and unreacted components of the feedstock. The product stream 4 is introduced into a distillation column 5 and fractionated into an overhead fraction and a bottoms fraction under a pressure of, for example, 1.6 bar. The operation in the distillation column 5 is conducted so that a mixture is withdrawn overhead containing essentially unreacted methanol and unreacted hydrocarbons (essentially C5 hydrocarbons) (conduit 6), while the bottoms fraction, withdrawn via a conduit 7, contains predominantly TAME. Part of the bottoms fraction is recycled in conduit 7a to reboiler 7b, and returned to the column 5. In addition, the bottoms fraction still contains higher alcohols and oligomers formed as a by-product during etherification.

The overhead fraction is cooled in a cooler 8 to a temperature below the single phase saturation temperature, the overhead fraction being liquefied during this step. The liquid mixture, excluding the fraction which is passed in conduit 6a via a condenser and conduit 6b back to the head section of the distillation column 5, is introduced into a tank 9 wherein the liquid mixture is separated into two liquid phases of differing densities. A heavier phase, rich in methanol, still containing 10–50%, preferably 25–40% hydrocarbons, is collected on the bottom of tank 9, a phase rich in hydrocarbons floating on top of the former phase. The tank 9 is designed as a decanter and permits separate removal of the two phases.

The methanol-rich phase is discharged via a conduit 10 and, without any intervening distillation to separate water from methanol (as shown in FIG. 1), admixed to the methanol feed stream 2. The phase rich in hydrocarbons is withdrawn via a conduit 11 and, if a residual content of methanol and hydrocarbons is permissible in the TAME, is admixed to the TAME-hydrocarbon mixture in conduit 7 via the conduit 15 shown in dashed lines (conduit 12). This is possible if the TAME is utilized for increasing the octane number of gasoline.

A portion of the hydrocarbon-rich fraction 11 can, in another version of the process, be introduced as reflux directly (as shown in FIG. 1) into the distillation column 5 by way of a conduit 13, likewise shown in dashed lines, in order to reduce the methanol content in the TAME-hydrocarbon mixture to be withdrawn as bottoms. In a further version of the process (not illustrated), the methanol content in the hydrocarbon-rich phase (conduit 11) can be reduced by a simple stripping column.

In a preferred process modification, a small amount of water is introduced via a conduit 14, also shown in dashed lines, into the overhead product from the distillation column 5. The water provides improved separation of the two phases and/or permits separation at a higher temperature in tank 9. The water passes practically completely into the methanol returned via conduit 10, affecting the etherification reactions to only a minor extent and resulting in the formation of higher alcohols removed together with the bottoms product from the distillation column.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated. Such examples refer to the reference numbers in FIG. 1.

EXAMPLE 1

Hydrocarbon Feed Stream (1):

Light gasoline fraction from a steam cracker having the following composition: content of reactive hydrocarbons: 7.8% by weight 2M-butene-1, 17.6% by weight 2M-butene-2.

(M represents methyl)

| Etherification: | temperature 70° C., pressure 15 bar |
|---|---|
| Molar ratio, methanol/reactive hydrocarbons | 1.1/1 |
| Total conversion: | about 65% |
| Selectivity: | about 90% |

Reaction Product (4):

19.2% by weight of TAME, 5.4% by weight of methanol, 75.1% by weight of hydrocarbons, 0.3% by weight of other products.

Distillation (5):

| % by Weight | Overhead Product | Bottoms Product |
|---|---|---|
| TAME | 0.1 | 93.6 |
| Methanol | 6.7 | 0.1 |
| Hydrocarbons | 93.2 | |
| Other products | — | 6.3 |
| Pressure (bar) | 2.1 | 2.5 |
| Temperature (°C.) | 54 | 110 |

Phase Separation (9):

Temperature −10° C., pressure 1.6 bar; 0.3% by weight of H$_2$O), based on the overhead product (6).

| % by Weight | Methanol Phase (*) | Hydrocarbon Phase |
|---|---|---|
| TAME | 0.1 | 0.1 |
| Methanol | 56.1 | 3.7 |
| Water | 3.6 | 0.1 |

(*) Recyling to etherification reactor 3, if necessary after drying

Etherification Product (7):

| TAME | 93.6% by weight |
|---|---|
| Methanol | 0.1% by weight |
| Hydrocarbons and other products | 6.3% by weight |
| RON (Research Octane Number), unleaded | 109 |
| MON (Motor Octane Number), unleaded | 98 |

EXAMPLE 2

Azeotropic Distillation (5):

| % by Weight | Overhead Product | Bottoms Product |
|---|---|---|
| TAME | 0.9 | 33.6 |
| Methanol | 11.8 | 0.3 |
| Hydrocarbons | 87.3 | |
| Other product | — | 66.1 |
| Pressure (bar) | 1.6 | 2.0 |
| Temperature (°C.) | 43 | 66 |

Phase Separation (9):

Temperature −10° C., pressure 1.6 bar; 1.3% by weight of H$_2$O, based on the overhead product (6).

| % by Weight | Methanol Phase (*) | Hydrocarbon Phase |
|---|---|---|
| TAME | 0.9 | 0.9 |
| Methanol | 57.7 | 4.5 |
| Water | 1.5 | 0.1 |

(*) Recycling to etherification reactor 3, if necessary after drying

The amount of hydrocarbons is markedly reduced as compared with Example 1.

Etherification Product (12):

| TAME | 20.6% by weight |
|---|---|
| Methanol | 1.7% by weight |
| Hydrocarbons and other products | 77.7% by weight |
| RON (Research Octane Number), unleaded | 102 |
| MON (Motor Octane Number), unleaded | 89 |

Figure 2:
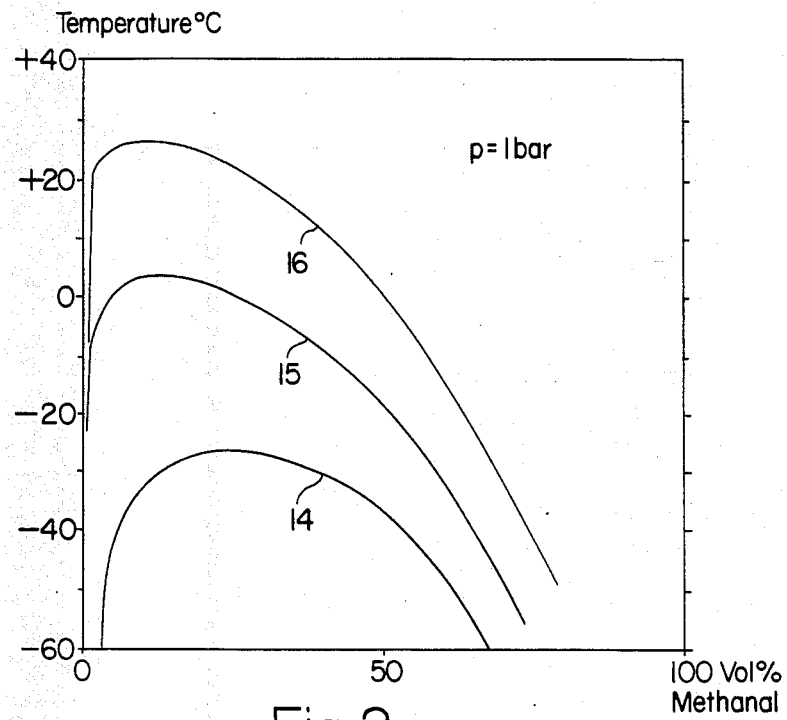
FIGS. 2 and 3 are phase diagrams.
Figure 3:
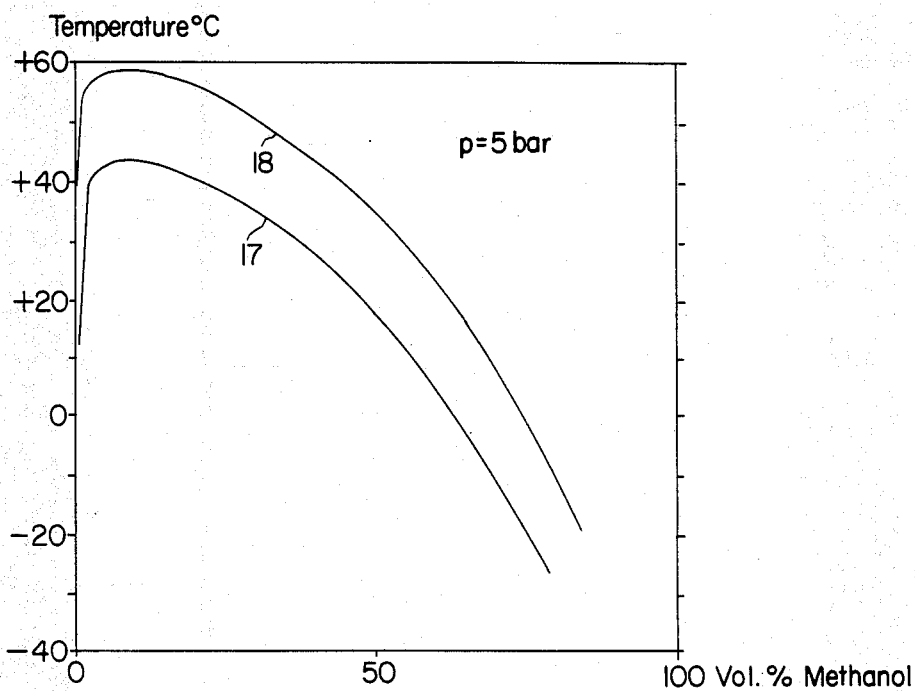

FIGS. 2 and 3 show the phase saturation curves separating the upper single phase mixture from the lower two-phase mixture for mixtures of methanol, the hydrocarbon feedstock (according to the numerical example), and water. The temperature is plotted over the methanol concentration of the stream 6 fed into tank 9 under pressures of 1 and 5 bar, respectively, and with the varying water contents set forth below:

| Curve No. | Water Content in Combined Streams (6) and (14) % by Weight |
|---|---|
| 14 | 0 |
| 15 | 0.15 |
| 16 | 0.30 |
| 17 | 0.45 |
| 18 | 0.60 |

It is necessary to subcool the oerhead stream to approximately 0° C.-59° C., preferably to 30° C., in order to form two immiscible phases.

The preceding examples can be repeated with similar success by substituting the generically or specifically described reactant and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the production of tertiary alkyl methyl ether (TAME) comprising etherifying a C$_5$ olefin-containing hydrocarbon feed stream with methyl alcohol in a reactor; fractionally distilling resultant reaction product formed during the etherifying into an overhead fraction containing essentially unreacted hydrocarbons and unreacted alcohol, and a bottom fraction containing essentially the ether; condensing the overhead fraction; and separating the alcohol from the condensed overhead fraction, the improvement which comprises cooling the condensed overhead fraction to below the single phase saturation temperature to form immiscible liquid phases, one containing essentially the alcohol and the other containing essentially the hydrocarbons, and withdrawing the immiscible phases separately from each other, with the provision that water is not added in said separating step to separate the alcohol from the C$_5$ hydrocarbon so as to form an aqueous phase containing the alcohol which is thereafter distilled into water and alcohol fractions.

2. A process according to claim 1 further comprising recycling at least part of the withdrawn immiscible phase containing essentially the alcohol into the etherification reactor.

3. A process according to claim 1 wherein said cooling of the overhead fraction is conducted in indirect heat exchange with a cold stream from a low-temperature gas separation facility.

4. A process according to claim 1 wherein said cooling of the overhead fraction, prior to separation of the two phases, is conducted to a temperature of −60° to +50° C.

5. A process according to claim 1 further comprising admixing a minor amount of water to the overhead fraction prior to phase separation in order to increase the separability of the immiscible phases, most of said water being passed into the liquid phase containing essentially alcohols and the remainder of said water passing into said liquid phase containing essentially the hydrocarbons.

6. A process according to claim 5 wherein the admixed proportion of water is between 0.01 and 2% by weight of the overhead fraction.

7. A process according to claim 5 further comprising recycling at least part of the withdrawn immiscible phase containing essentially the methyl alcohol into the etherification reactor without removing said water from said immiscible phase in an interventing step.

8. A process according to claim 5 further comprising passing at least a portion of the immiscible phase containing essentially the hydrocarbons directly into the fractional distillation zone as reflux liquid.

9. A process according to claim 8, wherein said cooling of the overhead fraction, prior to separation of the two immiscible phases, ranges to temperatures of about −43° to −60° C.

10. A process according to claim 1 wherein the distillation and the phase separation are conducted under a pressure of 1–20 bar.

11. A process according to claim 1 further comprising combining at least a portion of the immiscible phase containing essentially the hydrocarbons with withdrawn bottoms fraction from the fractional distillation step.

12. A process according to claim 1 further comprising passing at least a portion of the immiscible phase containing essentially the hydrocarbons directly into the fractional distillation zone as reflux liquid.

13. A process according to claim 1 wherein the feed stream is a light gasoline fraction from a thermal or catalytic cracking stage.

14. A process according to claim 1, wherein the bottoms fraction of the distillation column contains the ether in a mixture with a portion of the unreacted hydrocarbons.

15. A process according to claim 1 wherein the etherification is conducted at a temperature of +40° to −120° C. and under an absolute pressure of 1.2–20 bar.

16. A process according to claim 1, wherein said cooling of the overhead fraction, prior to separation of the two immiscible phases, ranges to temperatures of about −43° to −60° C.

17. A process according to claim 1, wherein distillation and phase separation are conducted under a pressure of about 1.5–3 bar.

18. A process according to claim 1, further comprising separating the ether from the bottoms fraction of the distillation.

19. A process according to claim 1, wherein at least part of the heat reaction liberated during etherification is employed to heat up at least a portion of the hydrocarbon feed stream passed into the reactor.

20. In a process for the production of tertiary amyl methyl ether (TAME) comprising etherifying an olefin-containing, essentially C$_5$ hydrocarbon feed stream with methyl alcohol in a reactor; fractionally distilling resultant reaction product formed during the etherifying into an overhead fraction containing essentially unreacted hydrocarbons and unreacted methyl alcohol and a bottom fraction containing essentially the ether; condensing the overhead fraction; and separating the methyl alcohol from the condensed overhead fraction, the improvement which comprises cooling the condensed overhead fraction to below the single phase saturation temperature to form only two immiscible liquid phases, one containing essentially the methyl alcohol and the other containing essentially the hydrocarbons, and withdrawing the immiscible phases separately from each other with the provision that water in a proportion of between 0.01 and 2% by weight of the overhead fraction is admixed to the overhead fraction prior to phase separation, said water providing increased separability of the two immiscible phases and most of the water transferring into the methanol phase upon condensation, said water being present in said methanol phase in a substantially smaller weight proportion compared to the methanol.

* * * * *